US012755816B2

(12) United States Patent
Kondo et al.

(10) Patent No.: US 12,755,816 B2
(45) Date of Patent: Oct. 6, 2026

(54) ANALYSIS APPARATUS AND ANALYSIS METHOD

(71) Applicant: NGK INSULATORS, LTD., Nagoya (JP)

(72) Inventors: Yoshio Kondo, Nagoya (JP); Kazunari Yamada, Nagoya (JP)

(73) Assignee: NGK INSULATORS, LTD., Nagoya (JP)

( * ) Notice: Subject to any disclaimer, the term of this patent is extended or adjusted under 35 U.S.C. 154(b) by 456 days.

(21) Appl. No.: 18/317,265

(22) Filed: May 15, 2023

(65) Prior Publication Data

US 2023/0386616 A1 Nov. 30, 2023

(30) Foreign Application Priority Data

May 25, 2022 (WO) .................. PCT/JP2022/021472

(51) Int. Cl.
*G16C 20/70* (2019.01)
*G01N 21/35* (2014.01)
*G16C 20/30* (2019.01)

(52) U.S. Cl.
CPC ............. *G16C 20/70* (2019.02); *G01N 21/35* (2013.01); *G16C 20/30* (2019.02)

(58) Field of Classification Search
CPC ........ G16C 20/70; G16C 20/30; G01N 21/35; G01N 21/3577; G01N 21/82
See application file for complete search history.

(56) References Cited

FOREIGN PATENT DOCUMENTS

| | | | | |
|---|---|---|---|---|
| CA | 2 441 931 A1 | | 10/2002 | |
| JP | 2020166706 A | * | 10/2020 | ............ G16C 20/70 |
| WO | 2006/122191 A2 | | 11/2006 | |
| WO | 2020/203922 W | | 10/2020 | |
| WO | 2022/013919 A1 | | 1/2022 | |

OTHER PUBLICATIONS

M.A. Neumann, "Combined crystal structure prediction and high-pressure crystallization in rational pharmaceutical polymorph screening", Jul. 22, 2015, Nature Communications (Year: 2015).*

(Continued)

*Primary Examiner* — Yossef Korang-Beheshti
(74) *Attorney, Agent, or Firm* — MATTINGLY & MALUR, PC

(57) ABSTRACT

An analysis apparatus includes: an acceptance unit adapted to accept parameters that affect precipitation of a crystal of an analyte; a prediction unit adapted to predict a type of crystal form to be precipitated, based on the accepted parameters; an evaluation unit adapted to evaluate a relationship between the type of crystal form to be precipitated and the parameters, based on a degree of influence that represents an extent to which each of the parameters affects the precipitation of the crystal of the analyte; and a providing unit that provides the type of crystal form to be precipitated and a precipitation condition to a user as information about a crystal form of a crystal to be precipitated. Thus, the type of crystal form to be precipitated and precipitation conditions of each crystal form can be predicted, with regard to an analyte that exhibits crystal polymorphism.

11 Claims, 7 Drawing Sheets

(56) References Cited

OTHER PUBLICATIONS

John Kendrick, "Crystal Structure Prediction of a Flexible Molecule of Pharmaceutical Interest with Unusual Polymorphic Behavior", Jan. 3, 2013, Crystal Growth and Design (Year: 2013).*
Patrick McArdle, "A method for the prediction of crystal structure of ionic organic compounds—the crystal structures of o-toluidinium chloride and bromide and polymorphism of bicifadine hydrochloride", Sep. 8, 2004, Royal Society of Chemistry (Year: 2004).*
Sarah Price, "Crystal Structure Prediction and Polymorphism", Transactions of the American Crystallographic Association, vol. 39, 2004 (Year: 2004).*
International Search Report of PCT/JP2022/021472 dated Jul. 5, 2022.
Written Opinion PCT/JP2022/021472 dated Jul. 5, 2022.
M.A. Neumann et al., "Combined crystal structured prediction and high-pressure crystallization in rational pharmaceutical polymorph screening", Nature Communications, Jul. 22, 2015, p. 1-7.
K. Igarashi "Crystallization operation and apparatus for highly controlling crystal characteristics", on line, Sep. 2013, pp. 3-4, [retrieved on Jun. 22, 2022].
Toshiro Fukami Physical property evaluation method for solid pharmaceutical agent, Journal of Pharmaceutical Science and Technology, Japan, 2005, vol. 65, No. 4, pp. 239-242.
International Search Report received in corresponding International Application No. PCT/JP2023/016024 dated Jul. 4, 2023.
Written Opinion received in corresponding International Application No. PCT/JP2023/016024 dated Jul. 4, 2023.
Extended European Search Report received in corresponding European Application No. 23811535.6 dated Apr. 15, 2026.
Parks, C. et al., "Solubility curves and nucleation rates from molecular dynamics for polymorph prediction—moving beyond lattice energy minimization", Physical Chemistry Chemical Physics, 2017, pp. 5285-5295, vol. 19, No. 7.
Heng, T. et al., "Progress in Research on Artificial Intelligence Applied to Polymorphism and Cocrystal Prediction", ACS Omega, 2021, pp. 15543-15550, vol. 6, No. 24.
Johnston, A. et al., "Targeted crystallisation of novel carbamazepine solvates based on a retrospective Random Forest classification", Crystengcomm, 2008, pp. 23-25.
Chinese Office Action received in corresponding Chinese Application No. 2023800395681 dated Aug. 13, 2026

* cited by examiner

FIG. 3

S

| | CRYSTAL FORM | CONCENTRATION FACTOR | TEMPERATURE FACTOR | INFRARED FACTOR | OTHERS | SCORE | PREDICTION |
|---|---|---|---|---|---|---|---|
| CONTRIBUTION RATIO | | 0.9 | 0 | 0 | 0.1 | | |
| CONDITION 1 | F1 | 1.00 | 1.00 | 0.20 | 1.00 | 1.00 | F1 |
| | F2 | 0.67 | 0.80 | 0.40 | 0.67 | 0.67 | |
| | H1 | 0.33 | 0.67 | 0.60 | 0.33 | 0.33 | |
| | Q | 0.00 | 0.30 | 0.90 | 0.00 | 0.00 | |
| CONDITION 2 | F1 | 1.00 | 0.20 | 0.10 | 0.20 | 0.82 | F1 |
| | F2 | 0.67 | 0.40 | 0.20 | 0.40 | 0.64 | |
| | H1 | 0.33 | 0.60 | 0.30 | 0.60 | 0.36 | |
| | Q | 0.00 | 0.90 | 0.40 | 0.90 | 0.09 | |
| CONDITION 3 | F1 | 1.00 | 1.00 | 0.20 | 0.10 | 0.91 | F1 |
| | F2 | 0.67 | 0.50 | 0.40 | 0.20 | 0.69 | |
| | H1 | 0.33 | 0.40 | 0.60 | 0.30 | 0.36 | |
| | Q | 0.00 | 0.10 | 0.90 | 0.40 | 0.04 | |
| ⋮ | ⋮ | ⋮ | ⋮ | ⋮ | ⋮ | ⋮ | ⋮ |

FIG. 4A

SUBSTANCE NAME: FEBUXOSTAT

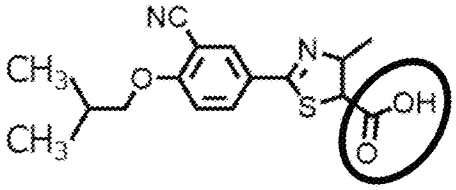

FUNCTIONAL GROUP THAT ABSORBS WAVELENGTH OF 3.2 μm

FIG. 4B (b) ■ALTERABLE CONDITIONS (1) SOLVENT TYPE
(2) INITIAL SUBSTANCE CONCENTRATION
(3) PRECIPITATION TEMPERATURE
(4) INFRARED WAVELENGTH

CRYSTAL FORMS TO BE PREDICTED
F1 (MOST STABLE)
F2 (HYDRATE)
Q
H1 (SUB-STABLE)

FIG. 4C

<EXAMPLE>

(1) SOLVENT: ETHANOL (2) 25,40[mL/mg] (3) CRYSTAL FORMS TO BE PRECIPITATED WERE PREDICTED AT 20,40,70[°C] UNDER A TOTAL OF SIX CONDITIONS (4) RADIATION WAVELENGTH: FIXED AT 3.2 μm

T

| ITEM CONTRIBUTION RATIO※1 | CONCENTRATION FACTOR | TEMPERATURE FACTOR | INFRARED FACTOR | OTHERS | DEGREE OF CONSISTENCY WITH EXPERIMENTS※2 | REMARKS |
|---|---|---|---|---|---|---|
| SCORING 1 | 0.90 | - | - | 0.10 | CONSISTENT: 1/6 PARTIALLY CONSISTENT: 3/6 | PREDICTED THAT F1 (MOST STABLE) WILL BE PRECIPITATED UNDER ALL CONDITIONS |
| SCORING 2 | 0.55 | 0.35 | - | 0.10 | CONSISTENT: 2/6 PARTIALLY CONSISTENT: 2/6 | PREDICTED THAT F1 WILL BE PRECIPITATED UNDER TWO CONDITIONS AND THAT F2 WILL BE PRECIPITATED UNDER FOUR CONDITIONS |
| SCORING 3 | 0.30 | 0.35 | 0.25 | 0.10 | CONSISTENT: 4/6 PARTIALLY CONSISTENT: 2/6 | PREDICTED THAT F1, F2, OR H1 WILL BE PRECIPITATED DEPENDING ON CONDITIONS |

ANALYSIS APPARATUS AND ANALYSIS METHOD

CROSS-REFERENCE TO RELATED APPLICATION

The present application claims priority from International Application PCT/JP2022/021472, filed on May 25, 2022, the content of which is hereby incorporated by reference into this application.

TECHNICAL FIELD

The present invention relates to technology that predicts types of crystal formations for a polymorphic analyte that can have multiple crystal forms using a precipitation process.

BACKGROUND ART

When an analyte is a polymorphic substance that can have multiple crystal forms, properties such as solubility vary with the crystal form, and thus it is desirable to be able to predict the crystal form to be precipitated. Conventionally, available methods for this include a method that involves microscopically calculating shapes of molecules under particular idealized conditions by quantum chemical calculation, and thereby predicting crystal structures themselves that can be realized. Conventional techniques also include a method for predicting energy of a crystal structure by machine learning.

According to Patent Literature 1, crystal structure candidates are selected from multiple crystal structure candidates, energy information about each of the selected crystal structure candidates is found by first-principle calculation, and of structure description information that represents crystal structure candidates, using structure description information corresponding to the selected crystal structure candidates as input information and using energy information about the selected crystal structure candidates as teacher information, machine learning is done to estimate energy information corresponding to the structure description information. A prediction apparatus for energy information of a crystal structure is disclosed that uses results of the machine learning produced by the above-mentioned machine learning means to estimate energy information corresponding to a crystal structure identified by the structure description information.

CITATION LIST

Patent Literature

[Patent Literature 1] Japanese Patent Laid-Open No. 2020-166706

SUMMARY OF INVENTION

Technical Problem

However, a crystal formation process is a complex and complicated physicochemical phenomenon. Besides, the crystal forms are vulnerable, in particular, to time variation during precipitation. Thus, it is difficult to predict crystal forms by calculation according to various conditions in the crystal formation process, including drying conditions and temperature conditions for precipitation of crystals.

That is, conventional processes have technical drawbacks that result in using a large amount of time.

For example, the present invention implements a technical solution that alleviates the burden on the identification of crystal forms by huge numbers of experimental trials.

For example, types of crystal forms are predicted with high accuracy by using combinations of physical conditions of a precipitation process, physical characteristics of parameters that affect the precipitation process, such as properties of the solvent and solute, and automatically evaluating the relationships between crystal forms and the parameters. In some implementations, accuracy of the predictions of the crystal forms may be further increased by changing the contribution ratios of the parameters based on determining a consistency between the predicted types of crystal forms and crystal forms actually precipitated.

Accordingly, the present invention is an improvement over conventional processes which huge numbers of experimental trials. Therefore, the technical solutions embodied in the present invention result in the advantage of providing more accurate crystal formation predictions in a shorter amount of time.

Accordingly, an object of the present invention is providing accurate predictions of the type of crystal form to be precipitated and precipitation conditions of each crystal form, with regard to an analyte that exhibits crystal polymorphism.

Solution to Problem

To solve the above problem, the present invention provides an analysis apparatus comprising: an acceptance unit adapted to accept parameters that affect precipitation of a crystal of an analyte to be analyzed for crystal polymorphism; a prediction unit adapted to predict a type of crystal form to be precipitated, based on an accepted structural formula and the accepted parameters; an evaluation unit adapted to evaluate a relationship between the type of crystal form to be precipitated and the parameters, based on a degree of influence that represents an extent to which each of the parameters affects the precipitation of the crystal of the analyte; and a providing unit adapted to provide the type of crystal form to be precipitated and a precipitation condition to a user as information about a crystal form of a crystal to be precipitated.

The present invention also provides an analysis method comprising: accepting parameters that affect precipitation of a crystal of an analyte; predicting a type of crystal form to be precipitated, based on the accepted parameters; evaluating a relationship between the type of crystal form to be precipitated and the parameters, based on a degree of influence that represents an extent to which each of the parameters affects the precipitation of the crystal of the analyte; and providing the type of crystal form to be precipitated and a precipitation condition to a user as information about a crystal form of a crystal to be precipitated.

Advantageous Effects of Invention

The present invention predicts the type of crystal form to be precipitated and precipitation conditions of each crystal form, with regard to an analyte that exhibits crystal polymorphism.

BRIEF DESCRIPTION OF DRAWINGS

FIG. 3 is a diagram showing an evaluation sheet used in estimating relationships between types of crystal form to be precipitated and parameters.

FIGS. 4A to 4C are diagrams showing search results for contribution ratios.

DESCRIPTION OF EMBODIMENTS

An embodiment of the present invention will be described in detail below with reference to the accompanying drawings.

According to the present embodiment, an analysis apparatus 10 accepts parameters that affect precipitation of crystals of an analyte. Then, based on the parameters, the analysis apparatus 10 predicts crystal forms produced when crystals are precipitated by drying a solution obtained by dissolving the analyte. Note that "crystal polymorphs" are compounds identical in chemical composition and different in crystal structure.

FIGS. 1A to 1E are diagrams showing examples of crystal polymorphs.

In FIG. 1, description will be given by citing febuxostat as an example of a substance that exhibits crystal polymorphism.

Febuxostat can take four crystal forms: F1 shown in FIG. 1A, F2 shown in FIG. 1B, H1 shown in FIGS. 1C, and Q shown in FIG. 1D. In each of the figures, the left side of the diagram shows a three-dimensional structure of the crystal form and the right side of the diagram shows a bonding state of molecules. Febuxostat has a structural formula shown in FIG. 1E.

Figure 1A:
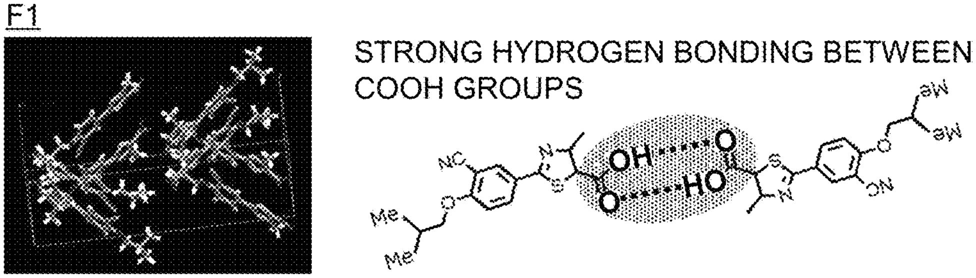
FIGS. 1A to 1E are diagrams showing examples of crystal polymorphs.

Of the crystal forms, the crystal form indicated by F1 in FIG. 1A, is formed by COOH groups (carboxy groups) of two molecules bonded together via strong hydrogen bonding, with the two molecules being bonded into a single mass.

Figure 1B:
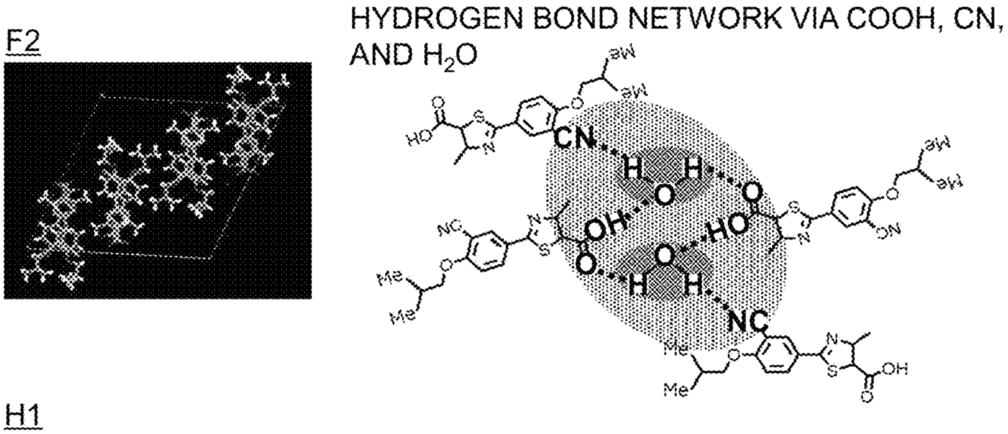

Also, the crystal form indicated by F2 in FIG. 1B forms a hydrogen bond network via COOH groups, CN groups (nitrile groups), and $H_2O$.

Figure 1C:
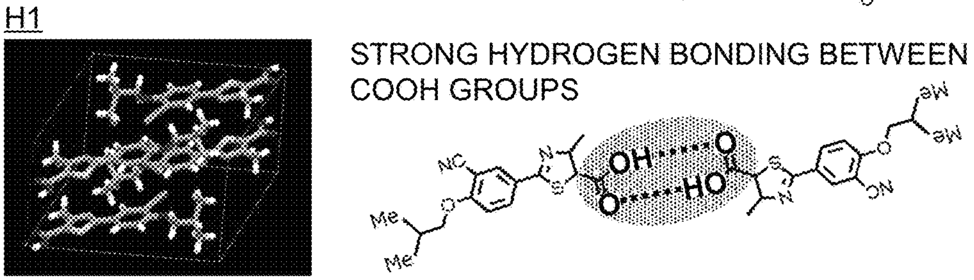

Furthermore, the crystal form indicated by H1 in FIG. 1C is formed by COOH groups (carboxy groups) of two molecules bonded together via strong hydrogen bonding, with the two molecules being bonded into a single mass as with FIG. 1A, but differs from FIG. 1A in crystal form.

Figure 1D:
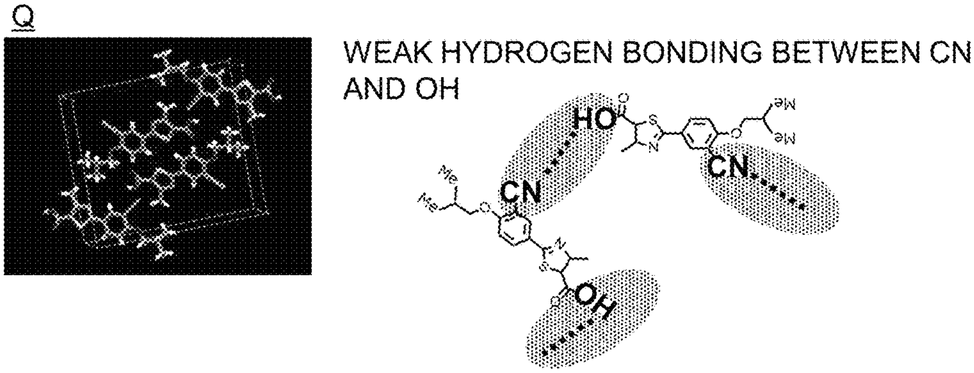
Figure 1E:
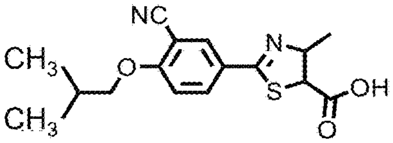

The crystal form indicated by Q in FIG. 1D is formed by a CN group and an OH group (hydroxyl group) bonded together via weak hydrogen bonding.

Note that by taking illustrated febuxostat as an example, description will be given below of cases in which crystal forms to be precipitated are predicted.

Note that in the present embodiment, the expression "crystal forms to be precipitated are predicted" does not mean calculating concrete crystal structures shown in FIGS. 1A to 1D, based on a molecular theory. Although details will be described later, it is not that the analysis apparatus 10 predicts crystal forms, but the analysis apparatus 10 predicts what nature of crystal forms, among multiple crystal forms, will be precipitated under given conditions. This also includes predictions as to whether a substance can take multiple crystal forms.

By taking illustrated febuxostat as an example, description will be given below of cases in which the types and precipitation conditions of crystal forms to be precipitated are predicted.

<General Description of Analysis Apparatus 10>

Figure 2:
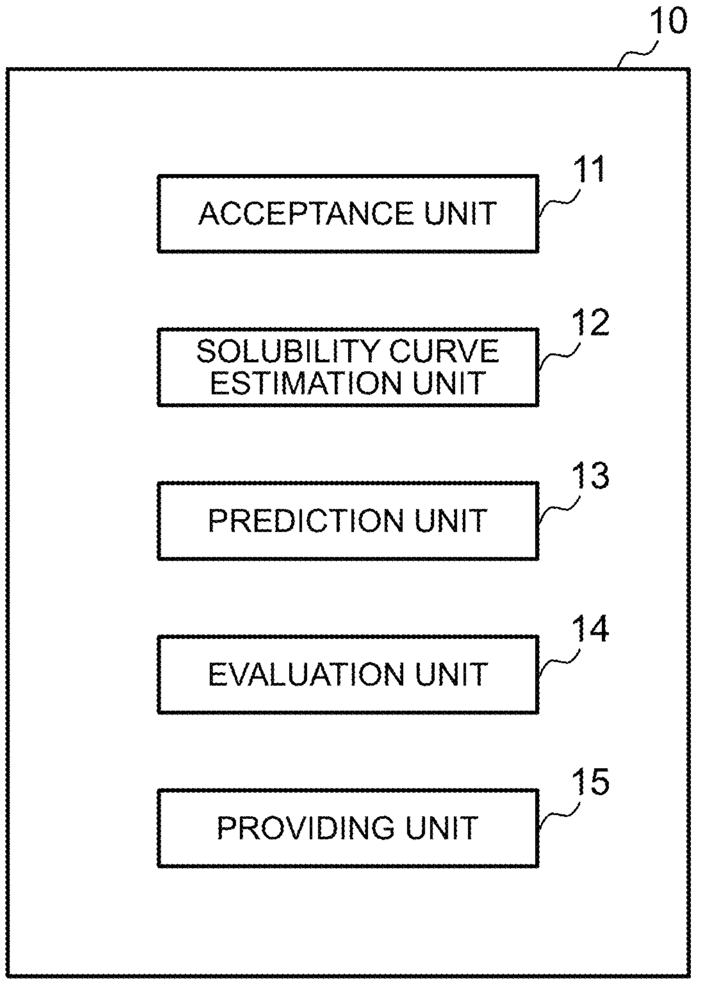
FIG. 2 is a block diagram showing a functional configuration of an analysis apparatus according to the present embodiment.

FIG. 2 is a block diagram showing a functional configuration of the analysis apparatus 10 according to the present embodiment.

The illustrated analysis apparatus 10 includes an acceptance unit 11, a solubility curve estimation unit 12, a prediction unit 13, an evaluation unit 14, and a providing unit 15.

The acceptance unit 11 accepts parameters that affect precipitation of crystals to be analyzed for crystal polymorphism. Here, the "parameters" are not specifically limited as long as they are indices that affect precipitation of crystals. The parameters include, for example, a structural formula of the analyte. The structural formula may be either a structural formula of an entire molecule or a structural formula known partially. For example, the structural formula may be the type of a functional group of a molecule. Besides, the parameters are, for example, conditions for a solution in dissolving the analyte in the solution, and then drying and crystalizing the analyte. Examples of the conditions for a solution include the type of solvent and concentration of the dissolved analyte. Furthermore, the parameters include precipitation conditions for use during the precipitation. Examples of the precipitation conditions include precipitation temperature, drying speed of the solvent, humidity, atmosphere, wavelength and intensity of infrared radiation, and structure of the precipitation apparatus.

The acceptance unit 11 also accepts tendency prediction, which is a prediction about a tendency of crystal forms expected to be precipitated. The tendency prediction is rough prediction about crystal forms likely to be precipitated, including, for example, the number and types of crystal forms that can be precipitated. If crystal forms that can be taken are known as shown in FIGS. 1A to 1E, the crystal forms can be used as they are for the tendency prediction.

On the other hand, if crystal forms that can be taken are unknown, the crystal forms can be found as follows. Examples of methods for tendency prediction include a method for predicting by comparison with similar substances. Available means for this include analyzing an analyte using DTA (Differential Thermal Analysis) or DSC (Differential Scanning calorimeter) analysis.

The solubility curve estimation unit 12 estimates a solubility curve of the analyte from tendency prediction.

To estimate the solubility curve of the analyte, for example, DSC analysis is conducted. Then, based on a melting point and heat of fusion found by the DSC analysis, the solubility curve can be formulated. This makes it possible to find the solubility curve with higher accuracy. Note that the solubility curve estimation unit 12 is not essential. Although the solubility curve has been described as being a function of the analysis apparatus 10, a solubility curve found experimentally may be inputted to the analysis apparatus 10.

The prediction unit 13 predicts the types of crystal form to be precipitated, based on accepted parameters.

Examples of items (INPUT) inputted to the prediction unit 13 include heater temperature, target wavelength, cooling method, initial temperature, and initial solvent concentration. The items inputted to the prediction unit 13 also include properties of the solvent. Examples of physical properties of the solvent include the type of solvent, absorption spectrum, density and specific heat, and vapor pressure constant. Furthermore, the items inputted to the prediction unit 13 include properties of a solute. Examples of physical properties of the solute include the type of solute, absorption spectrum, density and specific heat, and heat of fusion and melting point. Note that all of the above items are not necessary, and necessary items are selected from the above items.

According to the present embodiment, the prediction unit 13 uses, for example, infrared radiation energy of the analyte, infrared absorption energy of the analyte, product humidity, drying speed of the solvent, solvent concentration, solute concentration, solubility, degree of supersaturation, and the like as analysis indices. Note that all of the above items are not necessary, and necessary analysis indices are selected from the above items.

The analysis indices indicate what types of analysis are to be conducted based on input items. For example, the infrared radiation energy of the analyte and the infrared absorption energy of the analyte can be analyzed based on the heater temperature, the wavelength, the cooling method, and the like. By analyzing the infrared radiation energy of the analyte and the infrared absorption energy of the analyte, changes in the solution temperature and concentration at which the analyte will dissolve are predicted.

According to the present embodiment, from analysis results based on analysis indices, a final ratio of crystal 1/crystal 2 is found as an output (OUTPUT).

The prediction unit 13 also predicts the crystal forms to be precipitated, based on the estimated solubility curve. For example, based on the above-mentioned analysis indices, the prediction unit 13 predicts changes in the temperature and concentration of the solution containing the analyte. That is, the solubility curve varies with the crystal form. Then, by applying the analysis indices to the solubility curve for one of multiple crystal forms, the prediction unit 13 predicts whether the crystal form will be precipitated. By applying the analysis indices to the solubility curves for the other crystal forms, the prediction unit 13 also predicts whether the other crystal forms will be precipitated.

Based on a degree of influence that represents an extent to which each of the parameters affects the precipitation of the crystal of the analyte, the evaluation unit 14 estimates relationships between types of crystal forms to be precipitated and parameters. In so doing, the evaluation unit 14 uses an evaluation sheet S shown below.

FIG. 3 is a diagram showing an evaluation sheet S used in estimating relationships between types of crystal form to be precipitated and parameters.

Regarding the crystal forms predicted by the prediction unit 13 to be precipitated, the evaluation unit 14 finds the degrees of influence of the respective parameters. The degrees of influence represent extents to which each parameter affects the precipitation of respective crystal forms. The degree of influence is found for each crystal form. That is, the evaluation unit 14 finds the degree of influence that affects crystal precipitation of each crystal form on a parameter by parameter basis. The degree of influence may be said to be the likelihood of each crystal form to occur, i.e., weighting. On the illustrated evaluation sheet S, the degrees of influence are arranged in the column direction on a parameter by parameter basis.

On the illustrated evaluation sheet S, four parameters that affect crystal precipitation are listed: Concentration Factor, Temperature Factor, Infrared Factor, and Others. The concentration factor corresponds, for example, to initial substance concentration. The temperature factor corresponds to precipitation temperature. Furthermore, the infrared factor corresponds to infrared wavelength. Besides, scores such as 0.00, 0.33, 0.67, and 1.00 that represent degrees of influence are assigned to crystal forms of F1 (most stable), F2 (hydrate), H1 (sub-stable), and Q (unstable).

Contribution ratios (item contribution ratios) of these factors (parameters) in crystal precipitation are also set on the evaluation sheet S. The contribution ratio represents the degree to which each factor (parameter) contributes to the crystal form to be precipitated. The contribution ratio is set for each factor (parameter) such that the total contribution ratio of the four factors (parameters) will be 1. On the illustrated evaluation sheet S, the contribution ratios are arranged in the row direction. Specifically, the contribution ratios are set to 0.90, 0.00, 0.00, and 0.10.

Then, regarding each crystal form, the evaluation unit 14 multiplies the degrees of influence and the contribution ratio and adds up the resulting products for all the factors (parameters) to give a score. Then, using the scores as evaluation points, the evaluation unit 14 predicts that crystal forms with high evaluation points will be precipitated. The crystal form with the highest score or crystal forms with a score equal to or higher than a predetermined score may be predicted to be precipitated. It can be said that scores are assigned to crystal forms (evaluation points are calculated) according to the degrees of influence, that the crystal forms that can be precipitated are ranked, and that the crystal forms ranked high are predicted to be precipitated. Then, the evaluation unit 14 makes a similar prediction under each condition for precipitating crystals. In the illustrated example, predictions are made under Condition 1, Condition 2, . . . . Such conditions are set in precipitating crystals.

Then, the evaluation unit 14 compares the prediction results with the crystal forms precipitated under the respective conditions. Then, the evaluation unit 14 examines validity of the contribution ratio to be given by each factor (parameter) to the crystal form to be precipitated. It can be said that the evaluation unit 14 assigns scores based on the degrees of influence and the contribution ratios of the parameters, predicts the crystal forms to be precipitated, based on the results of scoring, and evaluates relationships between the types of crystal form to be precipitated and the parameters. It can also be said that the evaluation unit 14 compares the crystal forms predicted to be precipitated based on the results of scoring with the crystal forms actually precipitated under the same conditions and estimates the relationships between the types of crystal form to be precipitated and the parameters. Then, the evaluation unit 14 changes the contribution ratios based on the results of comparison and conducts searches to see how each factor (parameter) contributes to the crystal form to be precipitated. It can also be said that the evaluation unit 14 searches for contribution ratios based on the results of comparison.

FIGS. 4A to 4C are diagrams showing search results for contribution ratios.

Here, febuxostat having the structural formula shown in FIG. 4A was produced. FIG. 4B shows conditions set in precipitating crystals, including solution conditions and drying conditions. It is shown here that the solvent type in the solution can be changed. It is also shown that initial substance concentration can be changed. Furthermore, it is shown that precipitation temperature can be changed. Besides, infrared wavelength (wavelength of infrared radiation) can be changed. These are an example of above-mentioned parameters that affect crystal forms to be precipitated.

FIG. 4C shows results of searches conducted under six conditions selected from the alterable conditions shown in FIG. 4B. Here, ethanol is selected as Solvent Type, and two concentrations—25 [mL/mg] and 40 [mL/mg]—are selected as Initial Substance Concentration. Besides, 3.2 μm is selected as radiation wavelength. This wavelength is in the infrared wavelength region and corresponds to the absorption wavelength of a carboxy group surrounded by a solid line in FIG. 4A. Furthermore, three temperatures—20 [°C], 40 [°C], and 70 [°C]—are selected as Precipitation Temperature. That is, six conditions are created by combinations of the initial substance concentration and the precipitation temperature. Then, under the six conditions, the crystal forms predicted on the evaluation sheet S and the actually precipitated crystal forms are compared on the table in FIG. 4C.

In this case, four parameters—Concentration Factor, Temperature Factor, Infrared Factor, and Others—are considered as parameters that affect crystal precipitation. Concentration Factor corresponds to Initial Substance Concentration in FIG. 4B. Also, Temperature Factor corresponds to Precipitation Temperature. Furthermore, Infrared Factor corresponds to Infrared Wavelength.

Then, contribution ratios (item contribution ratios) of these factors (parameters) in crystal precipitation are set. The contribution ratios of the four factors (parameters) are configured such that their total will be 1.

The contribution ratios and degrees of influence of the parameters are shown in Table T by being evaluated using Scoring 1, Scoring 2, and Scoring 3.

In Scoring 1 of Table T, Concentration Factor is assigned 0.9 and Others is assigned 0.1. In so doing, it is assumed that the evaluation unit 14 predicts that the crystal form of F1 will be precipitated alone under all the conditions. Regarding the crystal forms actually precipitated, the crystal form of F1 is precipitated predominantly only under one condition. Under other three conditions, the crystal form of F1 is also precipitated, but not most predominantly. Note that under the other two conditions, the crystal form of F1 is not precipitated. Of the precipitated crystal forms, the crystal form precipitated the most is described as being "precipitated predominantly" crystal form. On the other hand, the crystal form which is precipitated, but not the most is described as being a "non-predominant" crystal form. On the evaluation sheet S, these states are described as being "Consistent: 1/6" and "Partially Consistent: 3/6," respectively.

In Scoring 2, Concentration Factor is assigned 0.55, Temperature Factor is assigned 0.35, and Others is assigned 0.1. In so doing, it is assumed that the evaluation unit 14 predicts that the crystal form of F1 will be precipitated alone under two conditions and that the crystal form of F2 will be precipitated alone under four conditions. Note that under the other two conditions, the crystal form of F1 is not precipitated. Regarding the crystal forms actually precipitated, the crystal forms of F1 and F2 are precipitated predominantly under two conditions. Under two other conditions, the crystal forms of F1 and F2 are also precipitated, but not most predominantly. On the evaluation sheet S, these states are described as being "Consistent: 2/6" and "Partially Consistent: 2/6," respectively.

In Scoring 3, Concentration Factor is assigned 0.30, Temperature Factor is assigned 0.35, Infrared Factor is assigned 0.25, and Others is assigned 0.1. In so doing, it is assumed that the evaluation unit 14 predicts that the crystal forms of F1, F2, and H1 will be precipitated in a mixture under all the conditions. Regarding the crystal forms actually precipitated, the crystal forms of F1, F2, and H1 are precipitated predominantly under four conditions. Under the other two conditions, the crystal forms of F1, F2, and H1 are also precipitated, but not most predominantly. On the evaluation sheet S, these states are described as being "Consistent: 4/6" and "Partially Consistent: 2/6," respectively.

In this way, according to the present embodiment, the evaluation unit 14 evaluates consistency between the crystal forms predicted based on the degrees of influence and the crystal forms actually precipitated. The degrees of influence are found using the solubility curve. Then, the evaluation unit 14 does scoring based on the degrees of influence as well as on the contribution ratios of the respective precipitation conditions (parameters) and evaluates the consistency between the crystal forms predicted to be precipitated based on the results of scoring and the crystal forms actually precipitated. Furthermore, based on the consistency, the evaluation unit 14 evaluates relationships between the types and precipitation conditions (parameters) of the crystal forms to be precipitated. Besides, based on the relationships, the evaluation unit 14 searches for contribution ratios. It can also be said that the evaluation unit 14 searches for contribution ratios based on the consistency between the crystal forms predicted to be precipitated based on the results of scoring and the crystal forms actually precipitated. In so doing, the evaluation sheet S is used according to the present embodiment. Using the evaluation sheet S, crystal forms are predicted by changing the contribution ratios and compared with the crystal forms actually precipitated. This clarifies the contribution ratios of the respective parameters. This makes it possible to predict what crystal forms will be precipitated under certain conditions. Note that not only the contribution ratios, but also the degrees of influence may be changed.

The providing unit 15 provides the types and precipitation conditions (confirmed parameters) of crystals to be precipitated to a user as information about the crystal forms of the crystals to be precipitated. In this case, the user is an operator of the analysis apparatus 10 or a provider of samples to be analyzed. Information about the crystal forms of the crystals to be precipitated concerns, for example, conditions that make it easy for intended crystal forms to be precipitated. Examples of such conditions include the initial concentration of a solution and drying conditions. Examples of such conditions also include crystal forms predicted to be precipitated when conditions are changed.

<Description of Effects>

The embodiment described above makes it possible to predict the types of crystal form to be precipitated, with regard to an analyte that exhibits crystal polymorphism. The embodiment also makes it possible to provide conditions for precipitating more useful crystal forms to the user. However, as described above, the present embodiment does not calculate concrete crystal structures based on a molecular theory. According to the present embodiment, there is no need to know crystal structures, and it is predicted that multiple crystal forms can be precipitated and predictions are made as to which of the multiple crystal forms will be precipitated.

A crystal formation process is a complex and complicated physicochemical phenomenon. Therefore, conventionally huge numbers of experimental trials are needed to prepare intended crystal forms. However, because of the capability to predict the types of crystal form to be precipitated, with regard to any analyte that exhibits crystal polymorphism, the present embodiment does not require such huge numbers of experimental trials.

According to the present embodiment, the prediction unit 13 runs numerical simulations using solubility curves and thereby predicts the crystal forms to be precipitated.

Whereas conventionally, for example, effects of infrared radiation on precipitation is not taken into consideration in predicting crystal forms to be precipitated, according to the present embodiment, the types of crystal form to be precipitated can be predicted by taking the effects of infrared radiation into consideration. Also, the types of crystal form to be precipitated can be predicted in response to not only infrared radiation, but also input of various parameters.

Furthermore, even if precipitation conditions or the like are changed, the types of crystal forms to be precipitated can be predicted quickly. In other words, the present embodiment can reduce the time and calculation cost needed in predicting crystal forms. That is, relationships between parameters and crystal forms to be precipitated become clear. Then, according to the present embodiment, when a solute, a solvent, and precipitation conditions are specified, crystal forms to be precipitated can be predicted based on the relationships. Besides, based on the relationships, a solute, a solvent, and precipitation conditions can be predicted when at least one type of crystal form is precipitated.

<Concrete Flow of Predicting Crystal Forms>

Next, a concrete flow of predicting crystal forms to be precipitated from a solution of a polymorphic analyte will be described in more detail.

Figure 5:
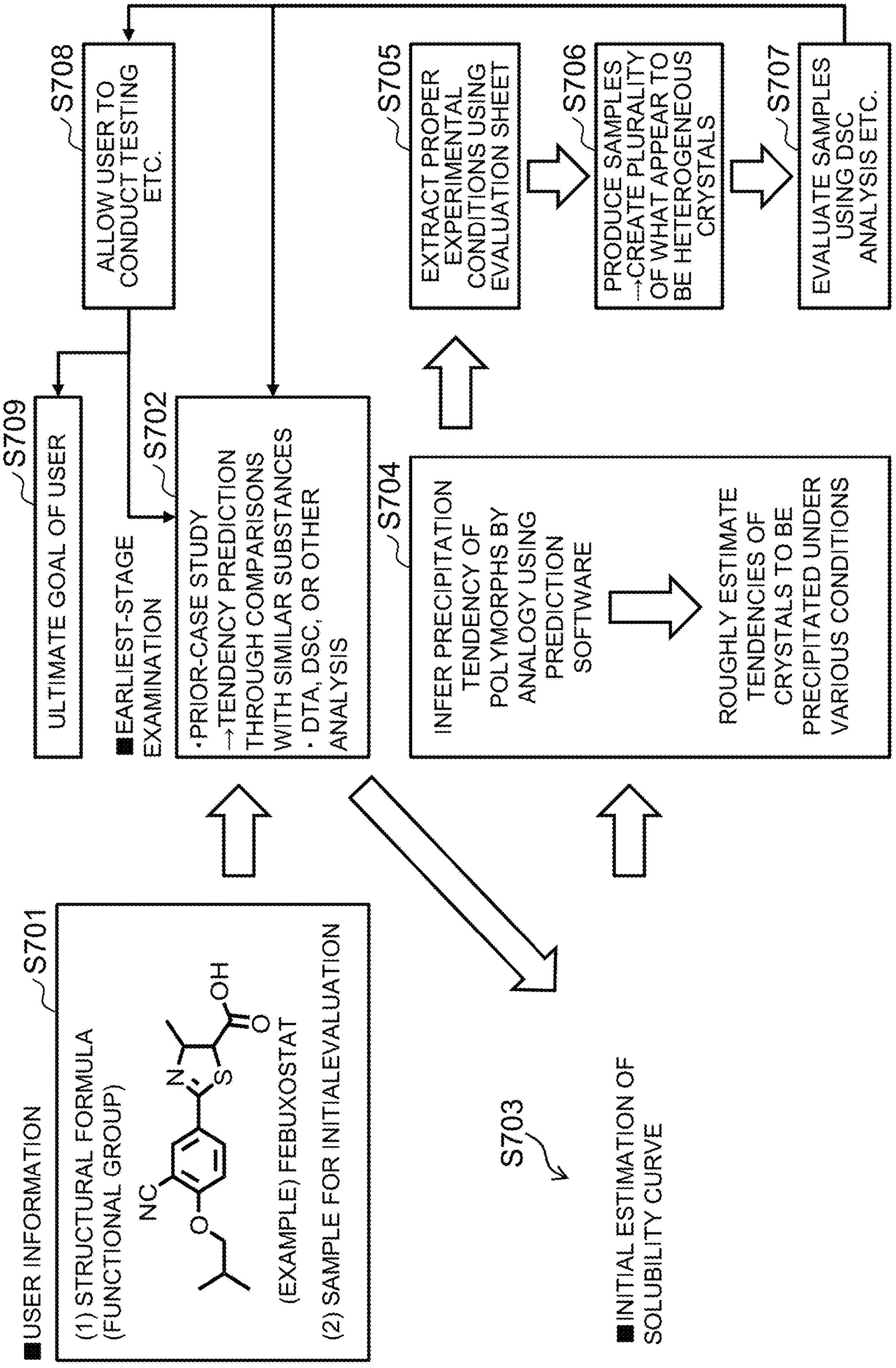
FIG. 5 is a diagram showing a sequential flow of predicting crystal forms according to the present embodiment.

FIG. 5 is a diagram showing a sequential flow of predicting crystal forms according to the present embodiment.

First, a structural formula of the analyte and a sample for initial evaluation are received as user information (step S701). Note that information about a functional group contained in the analyte may be used instead of the structural formula of the analyte. This makes clear the wavelength of infrared radiation absorbed during precipitation.

Next, a tendency prediction is made as an earliest-stage examination to predict a tendency of crystal forms expected to be precipitated and thereby predict crystal forms contained in the analyte (step S702). This can be done by making comparisons with similar substances through a prior-case study. The tendency prediction can also be made by conducting DTA or DSC analysis on samples received from the user.

Then, the acceptance unit 11 of the analysis apparatus 10 accepts the above information and the solubility curve estimation unit 12 makes an initial estimation of the solubility curve of the analyte (step S703). The solubility curve can be estimated through DSC analysis as described above.

Next, precipitation tendency of polymorphs is inferred by analogy using prediction software and tendencies of precipitating crystals under various conditions are roughly estimated (step S704). In the example described above, this corresponds to the process in which the prediction unit 13 runs simulations based on estimated solubility curves and predicts the types and percentage contents of the crystal forms to be precipitated.

Next, proper experimental conditions are extracted using the evaluation sheet S (step S705). In the example described above, this corresponds to the process in which the evaluation unit 14 determines contribution ratios using the evaluation sheet S. When the contribution ratios are determined, relationships between precipitation conditions (parameters) and crystal forms to be precipitated become clear.

Then, samples are produced actually (step S706). Consequently, a plurality of what appear to be heterogeneous crystals are created.

Furthermore, the produced samples are evaluated (step S707). This verifies whether intended crystal forms have been produced. The evaluation can be made using, for example, DSC analysis.

Then, the produced samples are provided to the user in order for the user to conduct testing or the like (step S708). The process can also return to step S702 to feed back the results for a tendency prediction.

This will allow the user to identify useful crystal forms (step S709).

Figure 6:
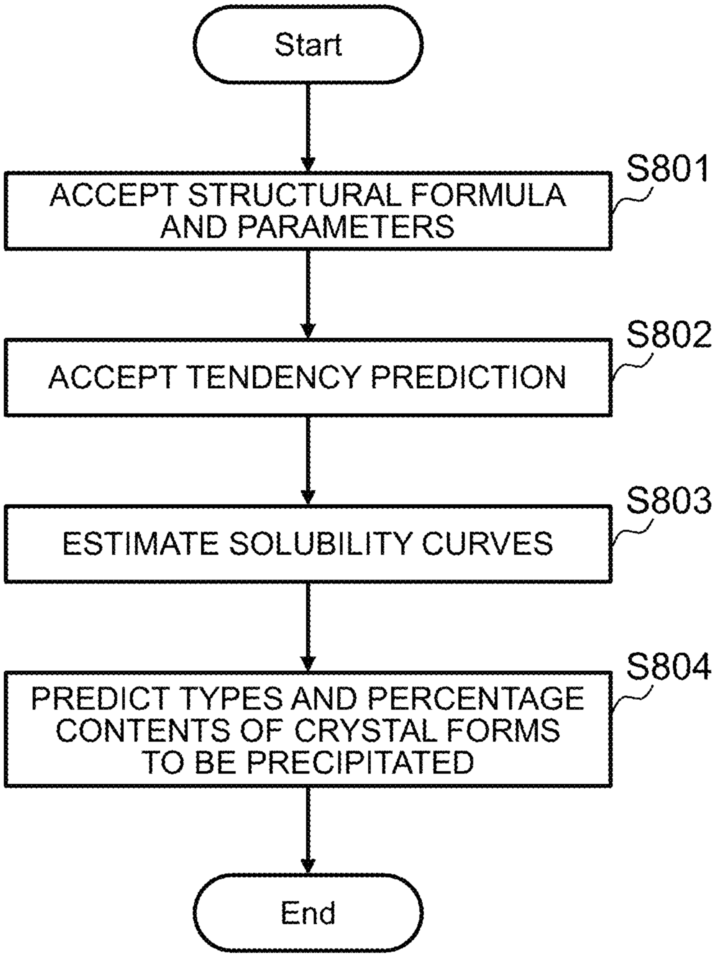
FIG. 6 is a flowchart illustrating an operation of the analysis apparatus in predicting crystal forms.

FIG. 6 is a flowchart illustrating an operation of the analysis apparatus 10 in predicting crystal forms. This corresponds to step S704 in FIG. 5.

First, the acceptance unit 11 accepts the parameters that will affect precipitation of the crystals of the analyte (step S801). The parameters are not specifically limited as long as they are indices that affect precipitation of the crystals as described above. In the example shown in the evaluation sheet S of FIG. 3, there are four parameters: Concentration Factor, Temperature Factor, Infrared Factor, and Others.

The acceptance unit 11 also accepts tendency prediction such as described in FIG. 5 (step S802).

Then, the solubility curve estimation unit 12 estimates solubility curves based on the parameters and tendency prediction accepted by the acceptance unit 11 (step S803).

Next, the prediction unit 13 runs simulations based on the estimated solubility curves and predicts the types and percentage contents of the crystal forms to be precipitated (step S804).

The process shown in FIG. 6 is implemented on a computer apparatus by collaboration between software and hardware resources. That is, a processor such as a CPU provided on the analysis apparatus 10 loads a program that implements functions of the analysis apparatus 10 from memory, executes the program, and thereby implements the functions.

Thus, the process in which the analysis apparatus 10 predicts crystal forms described above can be seen as a program that makes a computer implement an acquisition function of acquiring input data including the type of solute (analyte), the type of solvent that dissolves the solute, and precipitation conditions (parameters) under which the solute is caused to be precipitated as a crystal; and a prediction function of predicting crystal forms of crystals to be precipitated given the solute, the solvent and the precipitation conditions.

The process performed by the solubility curve estimation unit 12 can be seen as a function provided in the program, namely a solubility curve estimation function of estimating a solubility curve of the analyte. Based on the estimated solubility curve, the prediction function predicts the crystal forms to be precipitated.

Figure 7:
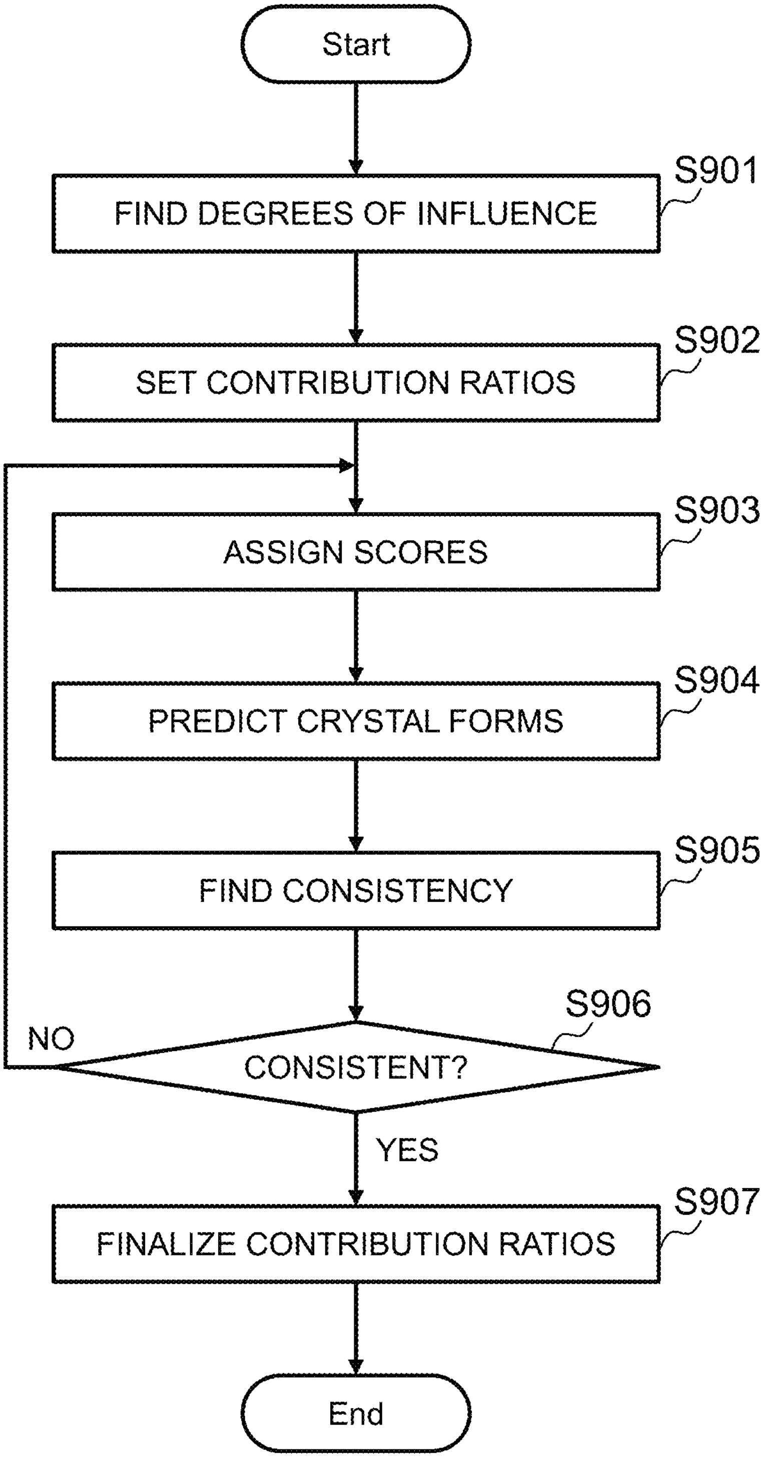
FIG. 7 is a flowchart illustrating an operation of the analysis apparatus in evaluating crystal forms.

FIG. 7 is a flowchart illustrating an operation of the analysis apparatus 10 in evaluating crystal forms. This corresponds to step S705 in FIG. 5.

First, based on the crystal forms predicted by the prediction unit 13 to be precipitated, the evaluation unit 14, finds the degrees of influence of the respective parameters (step S901).

Next, the evaluation unit 14 sets the contribution ratios that represent the extents to which respective parameters contribute to crystal precipitation (step S902).

Then, using the evaluation sheet S, the evaluation unit 14 assigns scores based on the degrees of influence and the contribution ratios of the parameters (step S903).

Furthermore, based on the results of scoring, the evaluation unit 14 predicts the crystal forms to be precipitated (step S904).

Next, the evaluation unit 14 compares the predicted crystal forms with the crystal forms actually precipitated under the same conditions and thereby finds consistency (step S905).

Then, the evaluation unit 14 determines whether the consistency satisfies a predetermined standard, meaning that the predicted crystal forms and the actually precipitated crystal forms are consistent with each other (step S906).

If the predetermined standard is satisfied as a result (Yes in step S906), the evaluation unit 14 finalizes the contribution ratios (step S907).

On the other hand, if the predetermined standard is not satisfied (No in step S906), the evaluation unit 14 returns to step S902 to set new contribution ratios such as for the parameter used to estimate the solubility curve, and performs step S903 and subsequent steps.

The process performed by the evaluation unit 14 of the analysis apparatus 10 according to the present embodiment is implemented on a computer apparatus by collaboration between software and hardware resources.

Thus, the process performed by the evaluation unit 14 of the analysis apparatus 10 according to the present embodiment can be seen as a program that makes a computer implement an acquisition function of acquiring input data including the type of solute (analyte), the type of solvent that dissolves the solute, and precipitation conditions (parameters) under which the solute is caused to be precipitated as a crystal; and an evaluation function of evaluating consistency between the predicted crystal forms and the actually precipitated crystal forms regarding the crystal forms of crystals to be precipitated given the solute, the solvent and the precipitation conditions.

Then, based on the consistency, the evaluation function of the program evaluates the relationships between the types and precipitation conditions of the crystal forms to be precipitated. Furthermore, when the solute, the solvent, and the precipitation conditions are specified, based on the relationships, the evaluation function can predict the crystal forms to be precipitated. Besides, based on the relationships, the evaluation function predicts a solute, a solvent, and precipitation conditions when at least one type of crystal form is precipitated. Here, when the evaluation unit 14 finalizes scoring for a certain substance, it is highly likely that the scoring can be applied to other substances of a similar molecular structure. Therefore, when this cycle is repeated predetermined times, the evaluation unit 14 can serve as the prediction unit 13. That is, in predicting crystal forms of a substance different from an evaluated solute, contribution ratios finalized via searching can be used.

When predicting which of multiple crystal forms will be precipitated, this program can improve prediction accuracy.

Note that the program that implements the present embodiment can be provided not only by means of communications, but also by being stored on a recording medium such as a CD-ROM.

<Modification>

Next, a modification of the analysis apparatus 10 will be described. According to the modification, the prediction unit 13 further predicts new crystal forms. This can be done, for example, by procedures (1) to (5) below.

(1) Regarding an analyte, a crystal form already known and regarded to be the most stable is set as the currently most stable crystal form. This crystal form is designated here, for example, as crystal form 1.

(2) Assuming that there exists a more stable unknown crystal form having higher stability, the crystal form is set as an imaginary crystal form. This crystal form is designated here, for example, as crystal form 2.

(3) Using a function of the evaluation unit 14, the ease of precipitation is compared between crystal form 1 and crystal form 2. If crystal form 2 is precipitated, the conditions under which crystal form 2 is precipitated are derived.

(4) Experiments of actually precipitating crystal form 2 are conducted under the derived conditions.

(5) If crystal form 2 is precipitated as a result of the experiments, this means that a new most stable crystal form has been found out. On the other hand, if crystal form 2 is not precipitated, it is highly likely that crystal form 1 is the most stable crystal form.

<Description of Analysis Method>

Here, the process performed by the analysis apparatus 10 can be seen as an analysis method that includes: accepting parameters that affect precipitation of a crystal of an analyte; predicting a type of crystal form to be precipitated, based on the accepted parameters; evaluating a relationship between the type of crystal form to be precipitated and the parameters, based on a degree of influence that represents an extent to which each of the parameters affects the precipitation of the crystal of the analyte; and providing the type of crystal form to be precipitated and a precipitation condition to a user as information about a crystal form of a crystal to be precipitated.

Whereas the present embodiment has been described above, the technical scope of the present invention is not limited to the scope of the embodiment described above. It will be apparent from the description of the claims that any form resulting from making various changes or improvements to the above embodiment is also included in the technical scope of the present invention.

REFERENCE SIGNS LIST

10: analysis apparatus; 11: acceptance unit; 12: solubility curve estimation unit; 13: prediction unit; 14: evaluation unit; 15: providing unit; S: evaluation sheet

The invention claimed is:

1. An analysis apparatus comprising:

a processor coupled to a memory, the memory storing instructions, that when executed by the processor, configure the processor to:

receive parameters that affect precipitation of a crystal of an analyte, the parameters including a structural formula of the analyte, predict a first type of crystal form to be precipitated, based on the accepted parameters, evaluate a relationship between the type of crystal form to be precipitated and the parameters, based on a degree of influence that represents an extent to which each of the parameters affects the precipitation of the crystal of the analyte, and provide the predicted type of crystal form to be precipitated and a precipitation condition to a user as information about a crystal form of a crystal to be precipitated; and after precipitating a crystal based on the parameters and the provided precipitation condition;

compare a form of the precipitated crystal with the predicted first type of crystal form:

change the contribution ratios based on the comparison; and predict a second type of crystal form to be precipitated based on the changed contribution ratios.

2. The analysis apparatus according to claim 1, wherein the processor is configured to predict the type of crystal form to be precipitated, based on a solubility curve of the analyte having the crystal form.

3. The analysis apparatus according to claim 2, wherein the processor is configured to generate the solubility curve, which is estimated based on a tendency prediction, which is a prediction about a tendency of the crystal form expected to be precipitated.

4. The analysis apparatus according to claim 1, wherein the parameters include a wavelength of infrared radiation used in precipitating a crystal.

5. The analysis apparatus according to claim 4, wherein a wavelength absorbed by the analyte having the crystal form expected to be precipitated is the wavelength of the infrared radiation.

6. The analysis apparatus according to claim 1, wherein the processor is configured to determine the degree of influence of each of the parameters based on the type of crystal form predicted by the prediction unit to be precipitated.

7. The analysis apparatus according to claim 6, wherein the processor is configured to determine scores for each of a plurality of crystal forms of the analyte based on the degrees of influence and contribution ratios of the parameters, predict the type of crystal form to be precipitated among the plurality of crystal forms of the analyte, based on the scores, and evaluate the relationship between the type of crystal form to be precipitated and the parameters.

8. The analysis apparatus according to claim 7, wherein the processor changes the contribution ratios of the parameters to different contribution ratios after predicting the crystal form to be precipitated and predicts a different crystal form to be precipitated based on the different contribution ratios.

9. The analysis apparatus according to claim 8, wherein the processor is configured to search for alternative contribution ratios based on a consistency between the predicted type of crystal form to be precipitated based on the scores and a crystal form actually precipitated.

10. The analysis apparatus according to claim 1, wherein the processor is configured to predict a new crystal form.

11. An analysis method comprising:

receiving parameters that affect precipitation of a crystal of an analyte, the parameters include a structural formula of the analyte;

predicting a first type of crystal form to be precipitated, based on the accepted parameters and contribution ratios of each of the parameters;

evaluating a relationship between the type of crystal form to be precipitated and the parameters, based on a degree of influence that represents an extent to which each of the parameters affects the precipitation of the crystal of the analyte;

providing the type of crystal form to be precipitated and a precipitation condition to a user as information about a crystal form of a crystal to be precipitated;

precipitating a crystal based on the parameters and the provided precipitation condition;

comparing a form of the precipitated crystal form with the predicted first type of crystal form;

changing the contribution ratios based on the comparison; and predicting a second type of crystal form to be precipitated based on the changed contribution ratios.

* * * * *